(12) United States Patent
Lin et al.

(10) Patent No.: US 9,134,633 B2
(45) Date of Patent: Sep. 15, 2015

(54) SYSTEM AND METHOD FOR DARK FIELD INSPECTION

(71) Applicant: Taiwan Semiconductor Manufacturing Company, Ltd., Hsin-Chu (TW)

(72) Inventors: Bo-Jiun Lin, Jhubei (TW); Hsin-Chieh Yao, Hsinchu (TW); Hai-Ching Chen, Hsinchu (TW); Tien-I Bao, Taoyuan County (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 23 days.

(21) Appl. No.: 14/138,743

(22) Filed: Dec. 23, 2013

(65) Prior Publication Data

US 2015/0179532 A1    Jun. 25, 2015

(51) Int. Cl.
*G03F 9/00* (2006.01)
*H01L 21/66* (2006.01)
*G01N 21/88* (2006.01)
*H01L 21/027* (2006.01)
*G01N 21/956* (2006.01)

(52) U.S. Cl.
CPC .......... *G03F 9/7069* (2013.01); *G01N 21/8806* (2013.01); *G01N 21/956* (2013.01); *H01L 21/027* (2013.01); *H01L 22/12* (2013.01); *G01N 2021/8825* (2013.01); *G01N 2021/95676* (2013.01); *G01N 2201/061* (2013.01); *G01N 2201/06113* (2013.01)

(58) Field of Classification Search
CPC ..... G03F 9/7069; H01L 22/12; H01L 21/027; G01N 21/8806; G01N 21/956; G01N 2021/95676; G01N 2021/8825; G01N 2201/06113; G01N 2201/061
USPC ....................................... 430/22, 30
See application file for complete search history.

(56) References Cited

U.S. PATENT DOCUMENTS 6,911,284 B2 * 6/2005 Rettenmaier et al. .............. 430/5
7,243,331 B2 * 7/2007 Bartov ............................ 716/52
8,559,001 B2 * 10/2013 Chang et al. ............... 356/237.5

* cited by examiner

*Primary Examiner* — Christopher Young
(74) *Attorney, Agent, or Firm* — Haynes & Boone, LLP

(57) ABSTRACT

The present disclosure provides a method for fabricating a semiconductor structure. The method comprises providing a substrate and a patterned layer formed on the substrate, one or more overlay marks being formed on the patterned layer; performing a pre-film-formation overlay inspection using a bright field (BF) inspection tool to receive a pre-film-formation data on the one or more overlay marks on the patterned layer; forming one or more layers on the patterned layer; performing a post-film-formation overlay inspection using a dark field (DF) inspection tool to receive a post-film-formation data on the one or more overlay marks underlying the one or more layers; and determining whether the pre-film-formation data matches the post-film-formation data.

20 Claims, 9 Drawing Sheets

Dark Field (DF)

Bright Field (BF)

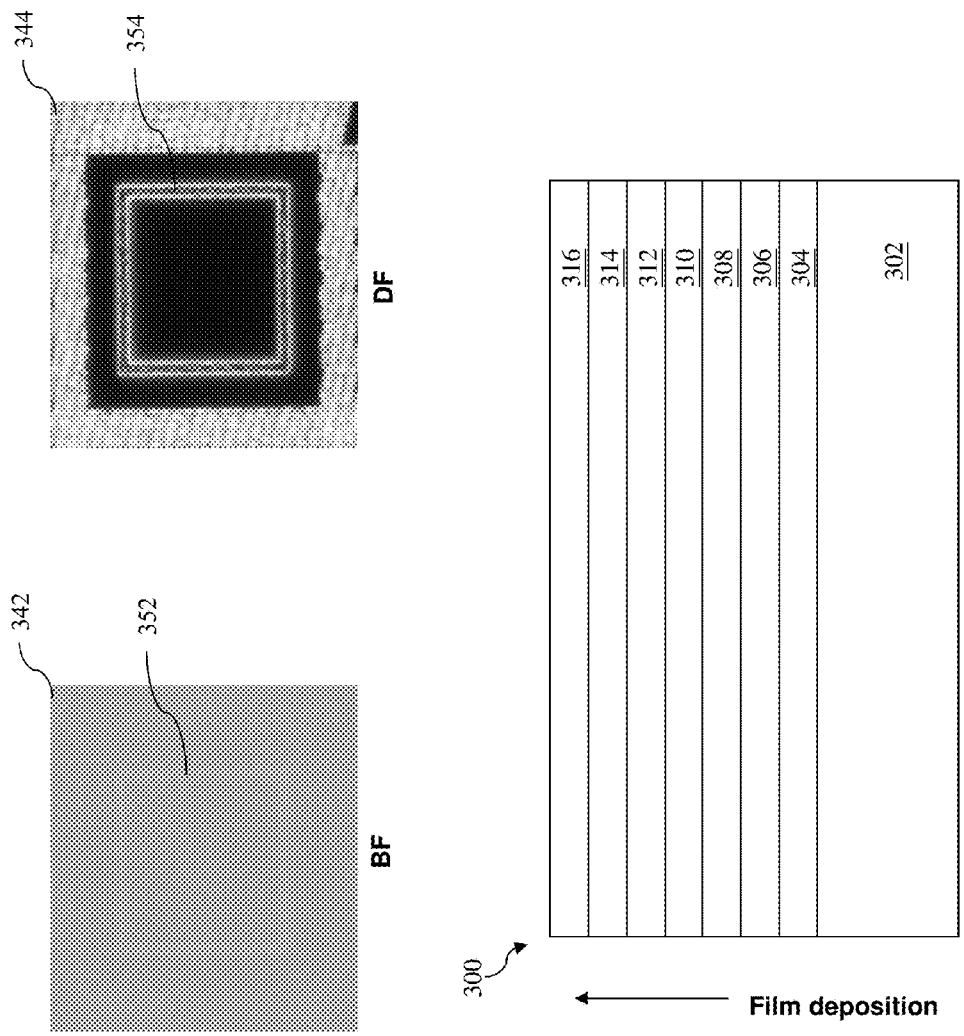

SYSTEM AND METHOD FOR DARK FIELD INSPECTION

BACKGROUND

Semiconductor integrated circuit (IC) technology has experienced rapid progress including the continued minimization of feature sizes and the maximization of packing density. The minimization of feature size relies on improvement in photolithography and its ability to print smaller features or critical dimensions (CD). This is further related to film deposition process and wafer alignment during lithography process. To improve the photolithography and film patterning accuracy, it is needed to measure the overlay mark errors generated from the wafer bending and/or deformation that may be caused by film deposition, thermal treatment, clamping (chucking) during wafer transferring, and other factors. However, after one or more film layers are deposited over the patterned layer, it may become difficult to measure the overlay marks on the patterned layer using the existing inspection tool.

Therefore, an apparatus for lithography patterning and a method utilizing the same are needed to address the above issues associated with overlay mark inspections.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIGS. 3A-3C are top view imaging results generated by the BF and DF inspection tools during inspections of the overlay marks on a patterned layer of a semiconductor structure fabricated at different stages according to some aspects of the present disclosure in one or more embodiments.

DETAILED DESCRIPTION

Figure 1:
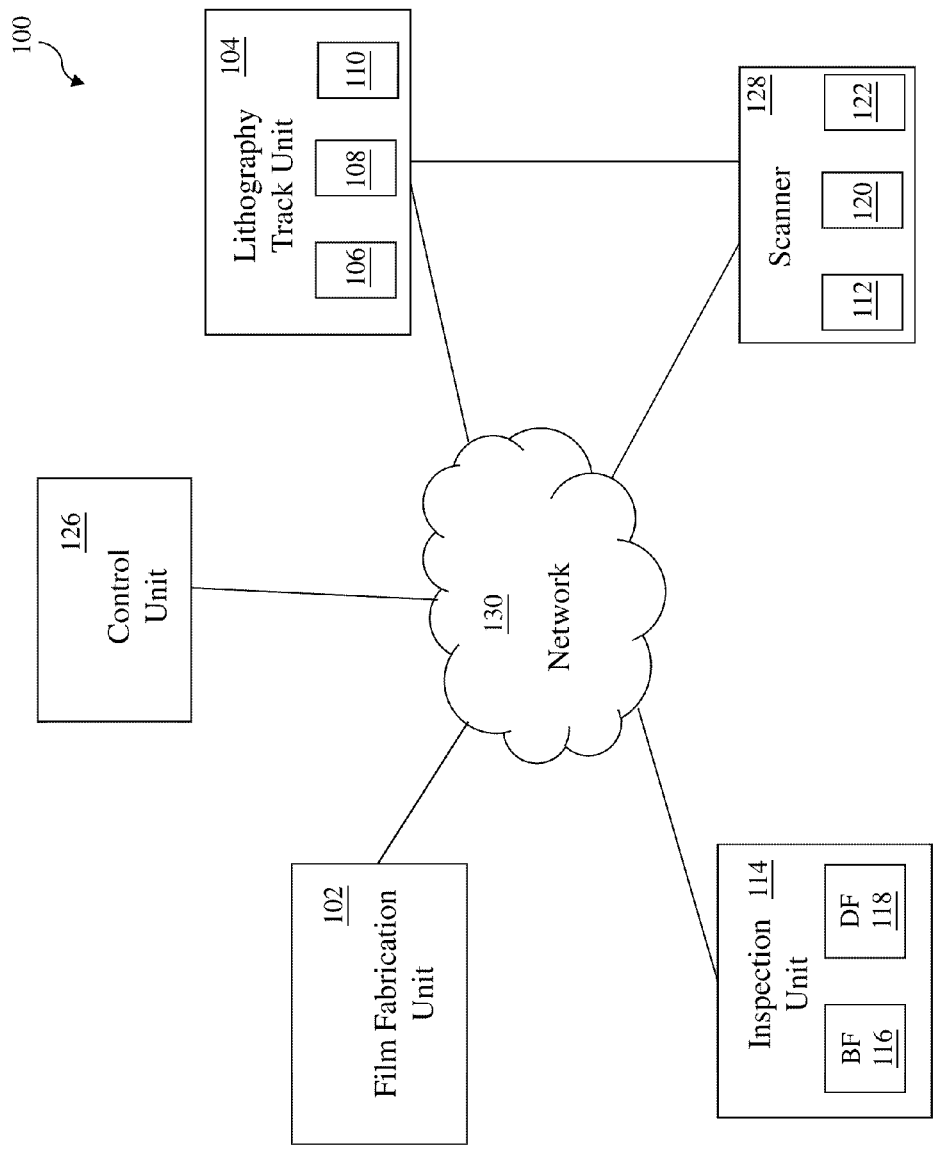
FIG. 1 is a block diagram illustrating a semiconductor fabrication system (a "system") for performing film deposition and lithography patterning processes constructed according to aspects of the present disclosure in one or more embodiments.

It is understood that the following disclosure provides many different embodiments, or examples, for implementing different features of the invention. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

FIG. 1 is a schematic block view of a semiconductor fabrication system 100 ("a system 100") for performing various film deposition and lithography patterning processes constructed according to various aspects of the present disclosure. As shown in FIG. 1, the system 100 includes various processing tools/units and metrology tools/units configured to perform various semiconductor structure fabrications, lithography processes including coating, alignment, exposure, baking, developing, other patterning, and/or inspection. Those processing tools and metrology tools are coupled to a network 130 and are collectively referred to as the system 100. For example as shown in FIG. 1, the system includes a film fabrication unit 102, a lithography track unit 104, an inspection unit 114, a control unit 126 and a scanner 128, each of which is coupled to the network 130. In some embodiments, the lithography track unit 104 and the scanner 128 are together named a lithography tool. However, each tool of the system 100 may be reconfigured, such as being reconfigured to be coupled with other lithography tools or be a part of another semiconductor fabrication system. The network 130 may be single network or may be a variety of different networks, such as an intranet and the internet, and may include both wireline and wireless communication channels.

Referring to FIG. 1, the system 100 includes a film fabrication unit 102 for fabricating one or more film layers in a semiconductor structure using various methods, such chemical vapor deposition (CVD), physical vapor deposition (PVD), atomic layer deposition (ALD), and spin-coating method. In some embodiments, the film deposition unit 102 includes one or more film fabrication tools, such as a CVD tool, a PVD tool, an ALD tool, and a spin-coating tool. The one or more film fabrication tools may be coupled together. The one or more film fabrication tools may also be independent from each other.

Referring to FIG. 1, the system 100 includes a lithography track unit 104 configured to perform lithography processing after one or more film layers are formed in the semiconductor structure. In some embodiments, the lithography track unit 104 is a processing tool that integrates various resist processing modules into one unit. The resist processing may include a coating module 106, a baking module 108, and a development module 110 according to some embodiments. In some embodiments, the resist processing includes more than one baking processes, such as a soft-baking, and a hard-baking, and the lithography track unit 104 includes more than one baking module designed or configured for baking processes at different temperatures, respectively. In some embodiments, the lithography track unit 104 is coupled with an exposure tool such that wafers can be exchanged between the lithography track unit 104 and the exposure tool.

Still referring to FIG. 1, the system 100 includes a scanner 128 including an exposure tool 112, and an alignment module 120. In some optional embodiments, the scanner also includes an overlay inspection tool 122. The exposure tool 112 is configured to expose a resist layer formed by the lithography track unit 104 on the semiconductor structure. In some embodiments, the exposure tool 112 includes a radiation source (illumination source) to generate radiation energy (or radiation beam) to expose the resist layer. The radiation energy may include any suitable light source, such as ultraviolet (UV) light, deep ultraviolet (DUV) light, extreme ultraviolet (EUV) light in various examples. The exposure tool 112 may be designed differently according to different characteristics of the radiation source and other factors. In some examples, the exposure tool 112 can be designed as an immersion lithography exposure module.

The exposure tool 112 may also include an illumination module with various optical components configured to image patterns on a mask onto the semiconductor structure. The illumination module may include multiple lenses and/or other optical components in various suitable configurations. In some embodiments, the exposure tool 112 may implement a one-shot exposure, or a step-and-exposure mode to form patterns of the mask repeatedly on a plurality of regions of a wafer. The mask used in the exposure process may include a transparent substrate and a patterned absorption layer. A light beam may be partially or completely blocked when directed on an absorption region. The absorption layer may be patterned to have one or more openings through which a light beam may travel without being absorbed by the absorption layer. The mask may incorporate other resolution enhancement techniques such as techniques using phase shift masks (PSM) and/or optical proximity correction (OPC). In some alternative embodiments where the radiation energy is EUV energy, the mask can be designed to have reflective mechanism. The mask may be secured on a mask state by a clamping mechanism (not shown), such as vacuum clamping or e-chuck clamping during the exposure process. The mask stage is designed and configured to be operable for translational, rotational, and/tilting motions according to the present embodiment.

The exposure tool 112 may also include a substrate stage that is capable of securing and moving the wafer to align the wafer with the mask. The substrate is secured on the substrate stage by a clamping mechanism, such as vacuum clamping or e-chuck clamping. In one embodiment, the substrate stage is further designed and configured to be operable for translational, rotational and/or tilting motions.

Still referring to FIG. 1, the scanner 128 also includes an alignment module 120. In some embodiments, the alignment module 120 is coupled to the lithography track unit 104. In some embodiments, the alignment module 120 is coupled to the exposure tool 112 such that the wafers through the alignment module 120 are sent to the exposure tool 112 for corresponding steps. Specifically, the alignment module 120 is coupled with the exposure tool 112 such that wafers can be transferred from the alignment module 120 to the exposure tool 112. The alignment module 120 is designed to perform an alignment measurement to the wafers. In some embodiments, the alignment process using the alignment module 120 includes measuring the alignment marks relative to a reference structure, such as a virtual grid, to define the alignment error. In one embodiment, the measured alignment error is used for a proper tuning process to reduce the alignment error and the overlay error. In some embodiments, the alignment process includes a post-coating overlay inspection where the overlay marks on the lithography mask are compared with the overlay marks formed on the patterned layer. In some embodiments, the number of the overlay marks on the lithography mask may not be the same as the number of the overlay marks formed on the patterned layer.

In some optional embodiments, the scanner 128 may include an overlay inspection tool 122 configured to perform an overlay inspection after the resist layer is patterned. For example, the overlay error is measured between the overlay marks on the patterned resist layer and on the underlying material layer on the wafer. In one embodiment, the overlay inspection tool 122 includes a position unit. In some embodiments, the scanner 128 is coupled to the lithography track unit 104. In some embodiments, the scanner 128 may stand alone.

Still referring to FIG. 1, the system 100 includes an inspection unit 114 configured to inspect the overlay marks on the patterned layer after forming one or more film layers over the patterned layer in the semiconductor structure. In some embodiments, the inspection unit 114 is used to perform overlay inspection after exposing the resist layer and/or after developing the exposed resist layer. In some embodiments, the overlay marks formed on the patterned layer may be first measured and mapped on the patterned layer. One or more film layers may be further formed on the patterned layer during the following processes. During the film formation processes, such as film depositions by CVD, PVD, and/or ALD, the thermal treatment and/or the film transferring process may induce wafer deformation, which may result in changes of the positions of the overlay marks. The inspection unit 114 may be used to monitor and map the positions of the overlay marks after the film formation processes and before the lithography process, so that the measured positions of the overlay marks can be used for the following alignment and overlay inspection during the lithography process. In some embodiments as shown in FIG. 1, the inspection unit 114 includes a bright field (BF) inspection tool 116 and a dark field (DF) inspection tool 118. In some embodiments, an overlay inspection tool may include a BF inspection mode and a DF inspection mode so that it is possible to perform overlay inspections by switching between the BF inspection mode and the DF inspection mode. In some embodiments, the system 100 may include a BF inspection tool and a DF inspection tool that are independent and separate from each other. For example, the BF inspection tool and the DF inspection tool are coupled to the network 130 respectively. The BF inspection tool and the DF inspection tool will be further discussed in detail later with respect to FIGS. 2A-2B in this current disclosure.

Still referring to FIG. 1, the system 100 may further include a control module 126 coupled to the network 130. In some embodiments, the control module 126 monitors the status of the lithography track unit 104, the scanner 128, and the film fabrication unit 102, and the inspection unit 114 by receiving data from the related units coupled to the network 130. The control module 126 may perform data analysis and calculate the overlay error, and then provide various instructions to the units via the network 120, such as instructions for adjusting film formation conditions, or instructions for adjusting lithography conditions in order to eliminate or reduce the overlay error. In some embodiments, the control module 126 may send instructions based on the alignment data from the alignment measurement. In some embodiments, the control module 126 may send instructions to tune the clamping mechanism of the respective position unit to reduce the chuck difference. In another embodiment, the control module 126 may send instructions to tune the wafer (or reticle) tilting, rotating. shifting and/or the imaging module of the exposure tool 112 to reduce the overlay error. In yet another embodiment, the control module 126 may send instructions to dynamically tune the exposure dose or imaging lens. In various embodiments, the control module 126 may include one or more computers configured to track and store the measured data from various units of the system 100. In some embodiments, the measurement data from different units may be stored in a computer readable media. Some common forms of the computer readable media used in the present invention may include, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, carrier wave, or any other medium from which a computer is adapted to read.

The various components of the system 100 may be arranged in any suitable configurations. The semiconductor fabrication system may further include other components to be coupled with other tools or components of the system 100 for performing various processes.

Figure 2B:
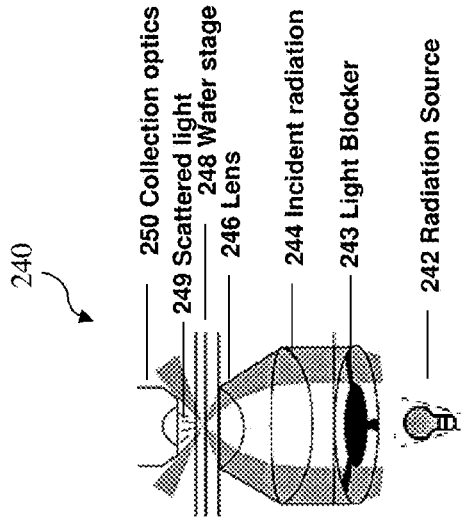
FIGS. 2A-2B are schematic diagrams comparing a bright field (BF) inspection tool with a dark field (DF) inspection tool according to aspects of the present disclosure in one or more embodiments.
Figure 2A:
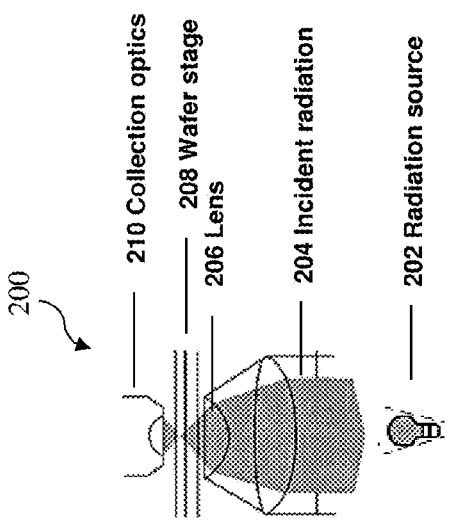

FIG. 2A is a schematic diagram illustrating the mechanisms of a bright field (BF) inspection tool 200 according to some aspects of the present disclosure. The BF inspection tool 200 can be used as the BF inspection tool 116 of FIG. 1. In some embodiments, the BF inspection tool 200 may be used as an optical microscope system, a scanning electron microscope (SEM) system, a scanning probe microscope system, laser microscope system, transmission electron microscope system, focus ion beam microscope system, or other suitable optical imaging systems. As shown in FIG. 2A, the BF inspection tool 200 includes a radiation source 202 configured to provide an incident radiation 204, a lens 206 configured to focus the incident radiation 204, a wafer stage 208 configured to hold the wafer that is being tested, and collection optics 210 configured to receive the optical signal and to collect the measured data.

In some embodiments, the radiation source 202 of the BF inspection tool 200 may provide the incident radiation 204 at one or more wavelengths in a wide electromagnetic spectrum (including but not limited to deep ultraviolet (DUV), ultraviolet (UV), visible light, infrared and the like). For example, the wavelengths of the incident radiation 204 may be in a range from about 10 nm to about 2000 nm. In one embodiment, the radiation source 202 provides the incident radiation 204 as an electron-beam (e-beam). In another embodiment, the radiation source 202 may be a laser providing the incident radiation 204 in the form of a laser beam. The incident radiation 204 may be focused by the lens 206 of the BF inspection tool 200 onto a surface of the wafer that is being loaded onto the wafer stage 208 as shown in FIG. 2A.

The BF inspection tool 200 further includes the wafer stage 208 configured to hold the wafer that is being measured by the BF inspection tool 100. The wafer may be mounted to the wafer stage 208 that allows for indexing and scanning of the wafer. In some embodiments of the present invention, the wafer may include a patterned layer formed over a substrate.

In some embodiments, the collection optics 210 mounted opposite the lens 206 may collect radiation transmitted by the wafer that is mounted on the wafer stage 208 and the collected data may be stored in a computer readable media by the computer 124. In some examples, the collected radiation may further be coupled to a photosensor for generating an image of the measured overlay marks on the patterned layer. It is to be understood that additional optical components may be included in the BF inspection tool 200 in addition to what is shown in FIG. 2A.

FIG. 2B is a schematic diagram illustrating the mechanisms of a dark field (DF) inspection tool 240 according to some aspects of the present disclosure. The DF inspection tool 240 can be used as the DF inspection tool 118 of FIG. 1. In some embodiments, the DF inspection tool 240 may be used such as an optical microscope system, a scanning electron microscope (SEM) system, a scanning probe microscope system, laser microscope system, transmission electron microscope system, focus ion beam microscope system, or other suitable optical imaging systems. As shown in FIG. 2B, the DF inspection tool 240 includes a radiation source 242 configured to provide an incident radiation 244, a lens 246 configured to focus the incident radiation 244, a wafer stage 248, and collection optics 250 that are substantially similar to the radiation source 202, the lens 206, the wafer stage 208 and the collection optics 210 of the BF inspection tool 200 as discussed in FIG. 2A.

The DF inspection tool further includes a light blocker 243 configured to block the center of the incident radiation beam 244 to produce a hollow cone of light. As shown in FIG. 2B, the hollow cone of light does not enter the collection optics 250 directly. During the DF inspection, light that is scattered by the wafer (e.g., scattered light 249) and enters the collection optics 250 can be collected. The DF inspection is advantageous to perform the image inspection with low contrast. In some embodiments, the light blocker 243 is made from a plastic material. In some embodiments, the light blocker 243 is made from a metallic material. The diameter ratio of the light blocker 243 to the incident radiation beam 244 maybe in a range from about 0.5 to about 0.9.

In some embodiments, the mechanisms explained in FIGS. 2A-2B are applicable in the BF inspection tool and the DF inspection tool of the system 100 as discussed with respect to FIG. 1. In some embodiments, the mechanisms of FIGS. 2A-2B are also applicable in a BF inspection mode and a DF inspection mode of an overlay inspection tool of the semiconductor fabrication system. In some embodiments, the BF inspection tool 200 and the DF inspection tool 240 may be integrated together in an inspection unit (e.g., the inspection unit 114 of FIG. 1), or the BF inspection mode and the DF inspection mode may be integrated together in an inspection tool. In some embodiments, the BF inspection tool 200 and the DF inspection tool 240 may be independent and separate from each other.

Figure 3A:
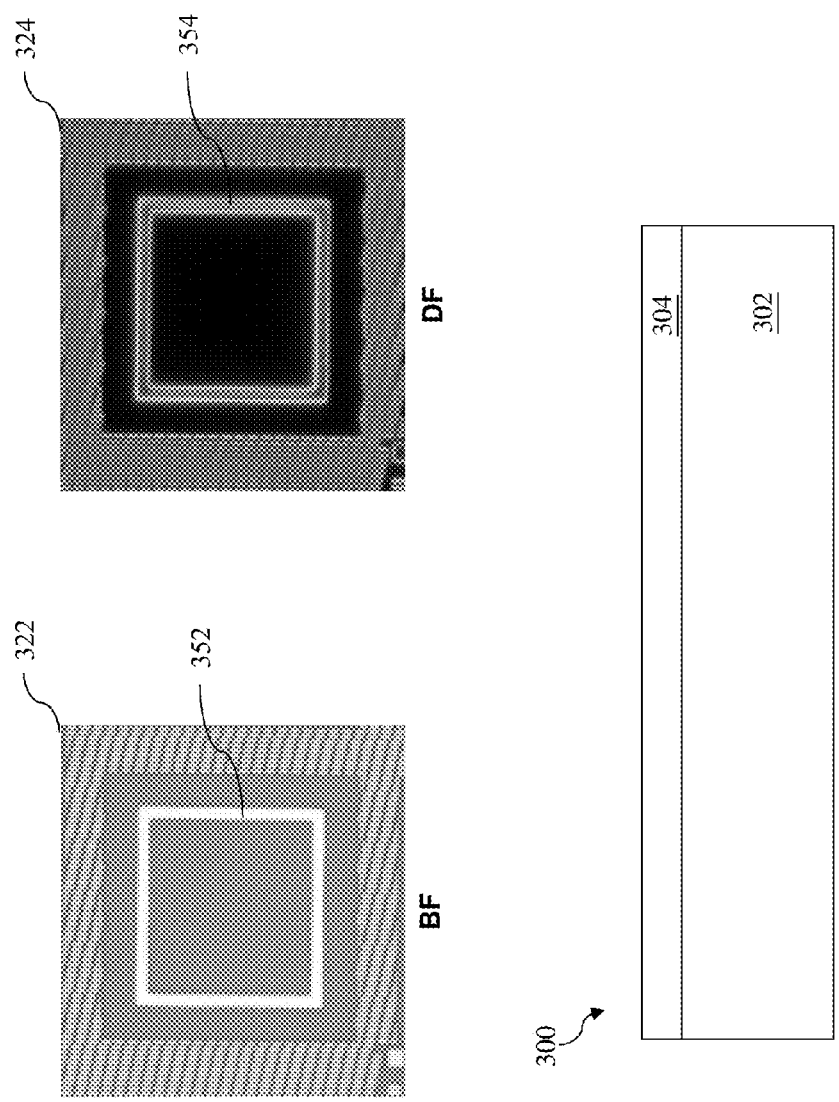

FIG. 3A shows a semiconductor structure 300 including a substrate 302 and a patterned layer 304 formed on the substrate 302. In some embodiments, the substrate 302 is an integrated circuit substrate (IC substrate), such as a semiconductor wafer (or wafer) having an elementary semiconductor such as crystal silicon, polycrystalline silicon, amorphous silicon, germanium, and diamond, a compound semiconductor such as silicon carbide and gallium arsenic, an alloy semiconductor such as SiGe, GaAsP, AlInAs, AlGaAs, and GaInP, or a combination thereof.

In some embodiments, the patterned layer 304 may be a patterned metal layer (e.g., a tungsten layer) or a patterned dielectric layer (e.g., an interlayer dielectric ILD layer). In some embodiments, the patterned layer 304 may also be formed as an upper portion of the substrate 302 (e.g., including shallow trench isolations STI). In some embodiments, one or more layers may be formed between the substrate 302 and the patterned layer 304. During the lithography patterning process of the layer 304, one or more overlay marks may be formed in the patterned layer 304 to monitor overlay deviation between the layers formed on the substrate.

FIG. 3A also shows a BF inspection view 322 including an overlay mark 352 generated by the BF inspection tool 200, and a DF inspection view 324 including an overlay mark 354 generated by the DF inspection tool 240, respectively. As shown in FIG. 3A, before forming other layers on the patterned layer 304, the overlay mark can be clearly observed in both the BF inspection view 322 and the DF inspection view 324.

Figure 3B:
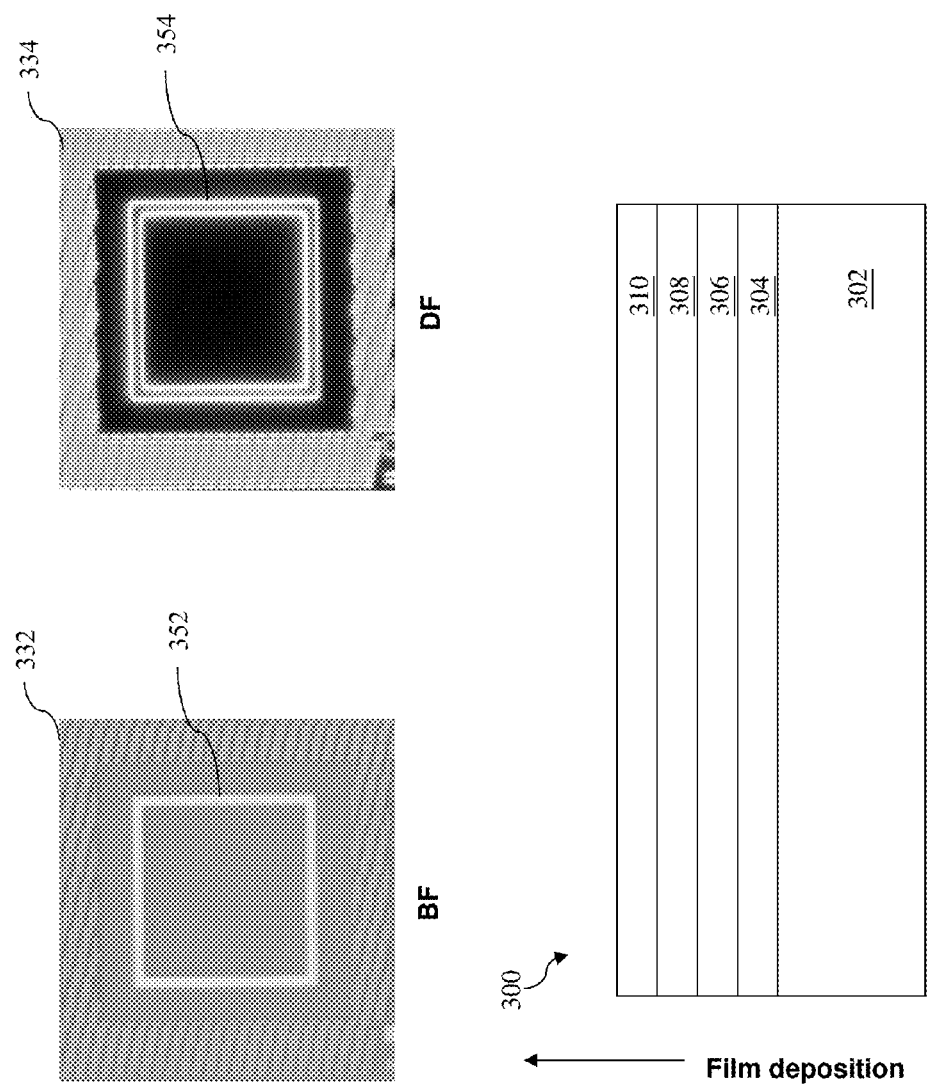

FIG. 3B shows a BF inspection view 332 generated by the BF inspection tool 200, and a DF inspection view 334 generated by the DF inspection tool 240 respectively after depositing one or more film layers on the patterned layer 304. In some examples, the one or more film layers may include an etching stop layer (ESL) 306, a low-k dielectric layer 308, and a first antireflective coating (ARC) layer 310 on the patterned layer 304. As shown in FIG. 3B, after forming the one or more film layers on the patterned layer 304, the overlay mark 352 may become less clear in the BF inspection view 332 due to the reduced image contrast. However, the DF inspection view 334 as shown in FIG. 3B may provide a clearer vision with sharper edges on the overlay mark 354.

FIG. 3C shows a BF inspection view 342 generated by the BF inspection tool 200, and a DF inspection view 344 by the DF inspection tool 240 respectively after further forming one or more film layers on the first ARC layer 310. In some examples, the one or more film layers may include a dielectric layer (e.g., a TiN layer) 312, a second ARC layer 314, and an amorphous silicon layer 316. In some embodiments, the amorphous silicon layer 315 is being patterned to form fin structures in the following lithography process. As shown in the BF inspection view 342 of FIG. 3C, after forming the amorphous silicon layer 316, the overlay mark 352 becomes unclear for data collection. In contrast, a clear vision of the overlay mark 354 with sharp edges is shown in the DF inspection view 344. This is due to the enhanced image contrast of the DF inspection mechanism. In some embodiments, one or more film layers, such as a hard mask layer, may be further formed on the amorphous silicon layer 316 before proceeding to the lithography process.

Figure 4A:
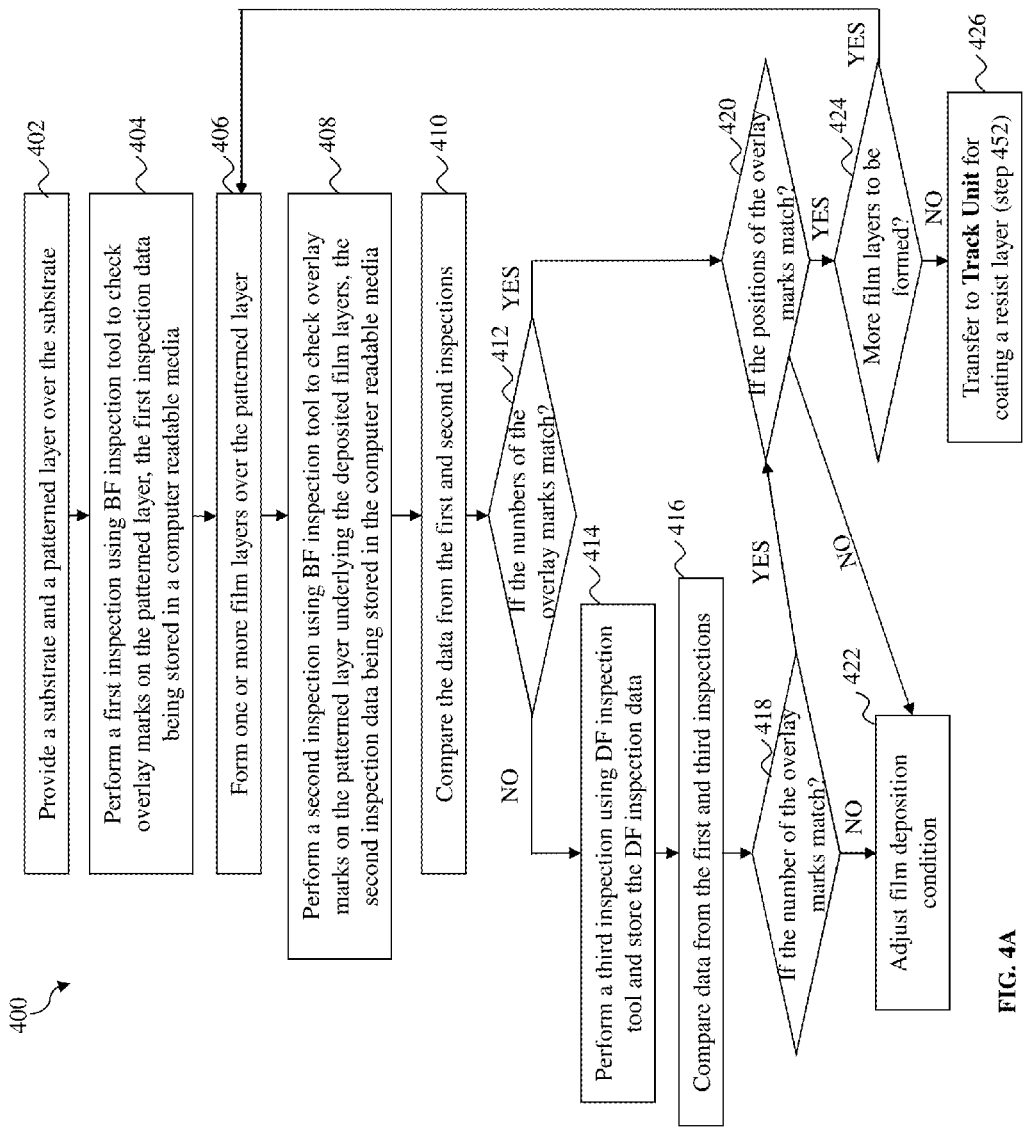
FIGS. 4A-4B are flowchart of methods for inspecting overlay marks before and after film depositions using semiconductor fabrication systems of FIG. 1 according to aspects of the present disclosure in one or more embodiments.

FIG. 4A is a flowchart of a method 400 for inspecting overlay marks during the formation of the one or more film layers using the system 100 of FIG. 1 according to one or more embodiments. In some embodiments, the method 400 for inspecting overlay marks on the patterned layer 304 is performed using the inspection unit 114 of FIG. 1. The one or more film layers on the patterned layer 304 may be formed using the film fabrication unit 102. Method 400 is described with reference to FIG. 4A, FIGS. 3A-3C, and FIG. 1. Method 400 begins at step 402 by providing a substrate 302 and a patterned layer 304 formed over the substrate 302. In some embodiments, one or more overlay marks are formed on the pattern layer 304 using a lithography process.

Method 400 proceeds to step 404 by performing a first inspection using the BF inspection tool 116 of FIG. 1. The first inspection is performed to check the number and positions of the overlay marks (e.g., overlay mark 352) on the patterned layer 304. The first inspection may be referred to as "pre-film-formation inspection". The overlay marks inspection results (pre-film-formation data) may include overlay position data and/or overlay mapping information. The overlay marks inspection results are stored in a computer readable media and provided to the control unit 126 via the network 130.

Method 400 proceeds to step 406 by forming one or more film layers (e.g., film layer 306, 308, 310. 312, 314, and/or 316) on the patterned layer 304. In some embodiments, the film layers are formed using the film fabrication unit 102 by any suitable film formation method, such as PVD, CVD, and/or ALD.

Method 400 proceeds to step 408 by performing a second inspection on the deposited film layers using the BF inspection tool 116. The second inspection is performed to check the number and positions of the overlay marks on the patterned layer 304 underlying the deposited film layers (e.g., film layer 306, 308, 310. 312, 314, and/or 316). The overlay marks inspection results from the second inspection are stored in a computer readable media and provided to the control unit 126 via the network 130.

Method 400 proceeds to step 410 by comparing the inspection data from the first inspection and the second inspection. In some embodiments, the number and/or the positions of the overlay marks from the first and the second inspections are compared.

Method 400 proceeds to step 412 to determine whether the numbers of the overlay marks from the first and second inspections match. When the numbers of the overlay marks from the first and second inspections are the same with each other, step 412 proceeds to step 420 by determining whether the positions of the overlay marks from the first inspection match with that of the second inspection. When the numbers of the overlay marks from the first and second inspections do not match, for examples, one or more overlay marks that are measured in the first inspection are unable to be observed in the second inspection, step 412 proceeds to step 414 by performing a third inspection using the DF inspection tool 240 (e.g., DF inspection tool 118). In some examples, the mismatch of the numbers of the overlay marks from the first and the second inspection may be caused by the reduced image contrast after forming one or more film layers on the patterned layer 304.

At step 414, the third inspection is performed to measure the number and positions of the overlay marks using the DF inspection tool 240. The overlay marks inspection results from the third inspection are stored in a computer readable media and provided to the control unit 126 via the network 130.

Method 400 proceeds to step 416 by comparing the inspection data from the third inspection and the first inspection. In some embodiments, the number and/or the positions of the overlay marks from the first and the third inspections are compared.

Method 400 proceeds to step 418 by determining whether the number of the overlay marks measured from the third inspection matches with that of the first inspection. When the number of the overlay marks from the first inspection matches that from the third inspection, step 418 proceeds to step 420 by determining whether the positions of the overlay marks from the first inspection match that of the third inspection. When the number of the overlay marks from the first inspection does not match that of the third inspection, for example, one or more overlay marks are unable to be observed using the DF inspection tool in the third inspection, method 400 proceeds to step 422 by adjusting the film deposition conditions. In some embodiments, the wafer deformation from the thermal treatment during film depositions may result in changes of the overlay marks on the patterned layer. Therefore, by adjusting the film deposition conditions, such as thermal treatment temperature and/or treatment time, the deformation of the wafer may be controlled so that the change of the number/position of the overlay marks stays within a predetermined margin of error. In some embodiments, the control unit 126 may process the data error, and provide instruction via the network 130 to the film fabrication unit 102 for adjusting the film deposition condition.

At step 422, it is determined whether the positions of the overlay marks from the second inspection or from the third inspection match with that of the first inspection. When the positions of the overlay marks from the second inspection or from the third inspection do not match with that of the first inspection due to, for example, the deformation of the wafer during the formation of the one or more film layers, step 420 proceeds to step 422 by adjusting the film deposition conditions. The control unit 126 may provide instructions for adjusting the film deposition condition. In some examples, the film deposition temperature and/or time may be adjusted to reduce the wafer deformation so that the change of the number/position of the overlay marks stays within a predetermined margin of error.

When the positions of the overlay marks from the second inspection or from the third inspection match with that of the first inspection, step 420 proceeds to step 424 by determining whether more film layers are to be formed on the patterned layer 304. When there are one or more film layers to be formed, step 424 proceeds to step 406 by forming one or more film layers over the pattern layer. When no more film layers are to be formed, step 424 proceeds to step 426 by transferring the semiconductor structure 300 to the lithography track unit 104 for coating a resist layer on the one or more formed film layers (e.g., step 452 of method 450 to be discussed layer in the present disclosure).

Figure 4B:
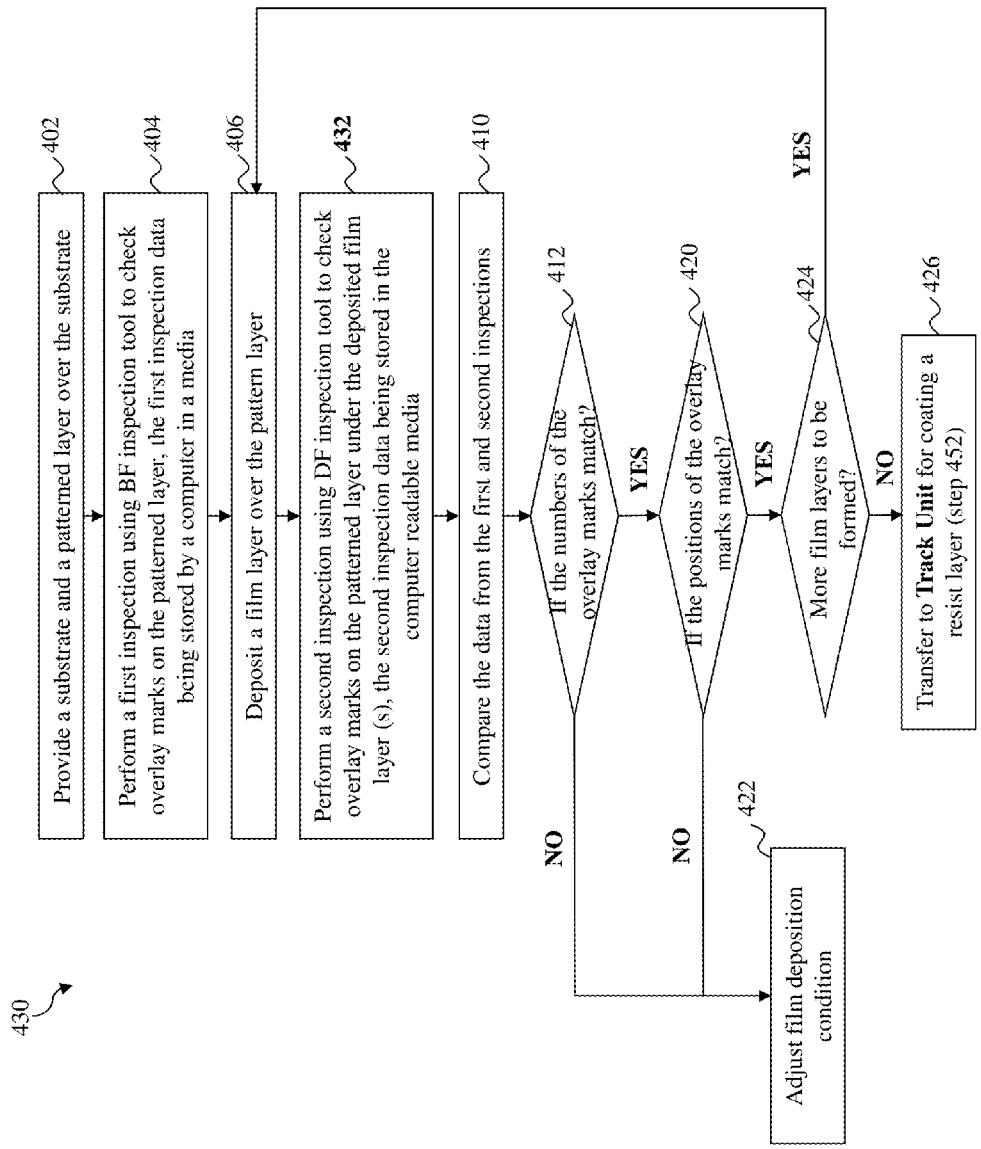

FIG. 4B is a flowchart of method 430 for inspecting overlay marks during the formation of the one or more film layers using the system 100 of FIG. 1 according to some embodiments of the present disclosure. In some embodiments, the method 430 is performed using the inspection unit 114 of FIG. 1. The one or more film layers on the patterned layer 304 may be formed using the film fabrication unit 102.

As shown in FIG. 4B, method 430 includes step 402 for providing a substrate 302 and a patterned layer 304 over the substrate 302, step 404 for performing a first overlay mark inspection using the BF inspection tool and storing the measured data, step 406 for forming one or more film layers on the patterned layer, step 432 for performing a second overlay mark inspection using the DF inspection tool and storing the measured data, step 410 for comparing the inspection data, step 412 for determining whether the numbers of the overlay marks from the first and second overlay mark inspections match, step 420 for determining whether the positions of the overlay marks from the first and second overlay mark inspections match, step 422 for adjusting the film deposition conditions, step 424 for determining whether more film layers are to be formed, and step 426 for transferring the semiconductor structure 300 to the lithography track unit 104 for coating a resist layer. In some embodiments, step 402, step 404, step 406, step 410, step 412, step 420, step 422, step 424, and step 426 of method 430 are substantially similar to the step 402, step 404, step 406, step 410, step 412, step 420, step 422, step 424, and step 426 of method 400.

After forming one or more film layers on the patterned layer at step 406, and different from method 400, at step 432 of method 430, a DF inspection using the DF inspection tool 240 is directly performed on the one or more formed film layers of the semiconductor structure 300. In some embodiments, step 432 of method 430 is performed using the DF inspection tool 118 as part of the inspection unit 114 as shown in FIG. 1.

Figure 4C:
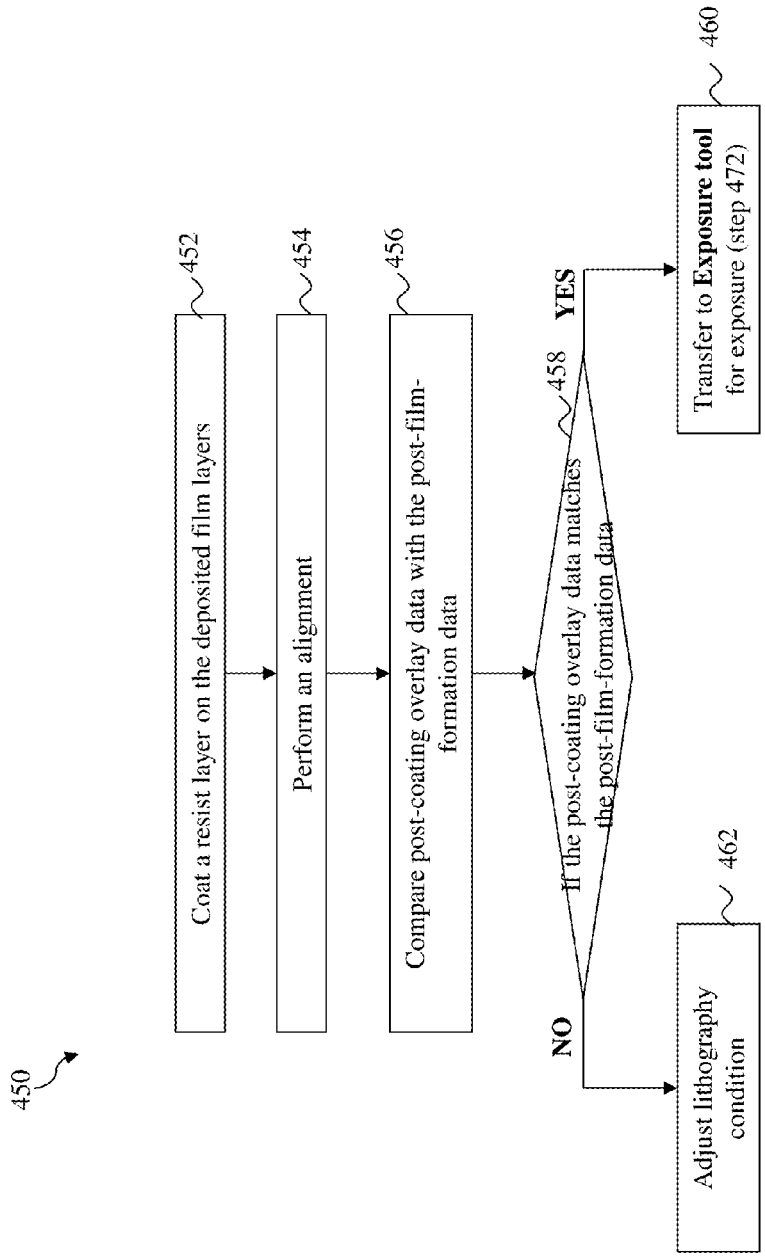
FIG. 4C is a flowchart of a method for comparing post-coating overlay data with the post-film-formation data measured using the semiconductor fabrication systems of FIG. 1 according to aspects of the present disclosure in one or more embodiments.

FIG. 4C is a flowchart of a method 450 for comparing post-coating overlay data with the post-film-formation data measured and stored using method 400 or method 430 according to aspects of the present disclosure in one or more embodiments. In some embodiments, method 450 is performed using the lithography track unit 104, scanner 128, and inspection unit 114 of system 100. After forming the one or more film layers on the patterned layer 304, the semiconductor structure 300 may be transferred to the lithography track unit 104 for performing a lithography process to form semiconductor features, such as fin structure, in the semiconductor structure 300.

Method 450 starts from step 452 by coating a resist layer on the top layer of the one or more formed film layers (e.g., the amorphous silicon layer 316). In some embodiments, the coating process at step 452 is performed using the coating module 106 of the lithograph track unit 104. In some embodiments after coating the resist layer, a soft baking is performed to the coated resist layer using the baking module 108 of the lithography track unit 104.

Method 450 proceeds to step 454 by performing an alignment to align the wafer with the lithography mask before exposure using the alignment module 120 of the scanner 128. In some examples, the alignment module 120 is a step-and-scan system, a scanning projection aligner, a contact aligner, a proximity aligner, a step-and-repeat aligner (stepper), and/or the like. In some embodiments, one or more alignment marks on the lithography mask are compared with the reference structure, such as a virtual grid. In some embodiments, one or more overlay marks on the lithography mask are compared with the overlay marks on the wafer to align the mask with the wafer for the following exposure. In some embodiments, the alignment measurement data is stored in a computer readable media and provided to the control unit 126 via the network 130. In some embodiments, the alignment measurement data includes a post-coating overlay data. For example, the post-coating overlay data may include information such as number and positions of the overlay marks on the lithography mask.

Method 450 proceeds to step 456 by comparing the post-coating overlay data with the overlay inspection data that are measured and stored using method 400 or method 430 as discussed earlier in the present disclosure. In some embodiments, the overlay inspection data are post-film-formation data that are measured after the one or more film layers are formed on the patterned layer and before the semiconductor structure 300 is transferred to the lithography track unit 104 to perform the lithography process. In some embodiments, the post-film-formation data is obtained using the DF overlay inspection tool or the BF overlay inspection tool. In some embodiments at step 456, the number and/or positions of the marks on the lithography mask are compared with the number and/or positions of the overlay marks from the post-film-formation data.

Method 450 proceeds to step 458 by determining if the post-coating overlay data matches the post-film-formation data. When the post-coating overlay data matches the post-film-formation data, step 458 proceeds to step 460 for transferring the coated semiconductor structure 300 to the exposure tool 112 of the scanner 128 for performing the exposure process on the coated resist layer (e.g., step 472 of method 470 to be discussed layer in the present disclosure). When the post-coating overlay data does not match the post-film-formation data, step 458 proceeds to step 462 by adjusting the lithography conditions. In some examples, the control module 126 may process the post-film-formation data and the post-coating overlay data, and provide instructions for adjusting the parameters and/or conditions of the lithography tracking unit 104 for compensating the error. In some examples, the control module 126 may provide instructions for adjusting the parameters of the coating module 106 or adjusting the conditions for the coating process via the network 130. In some examples, the control module 126 may provide instructions for adjusting the parameters of the baking module 108 or adjusting the conditions for the baking process via the network 130.

Figure 4D:
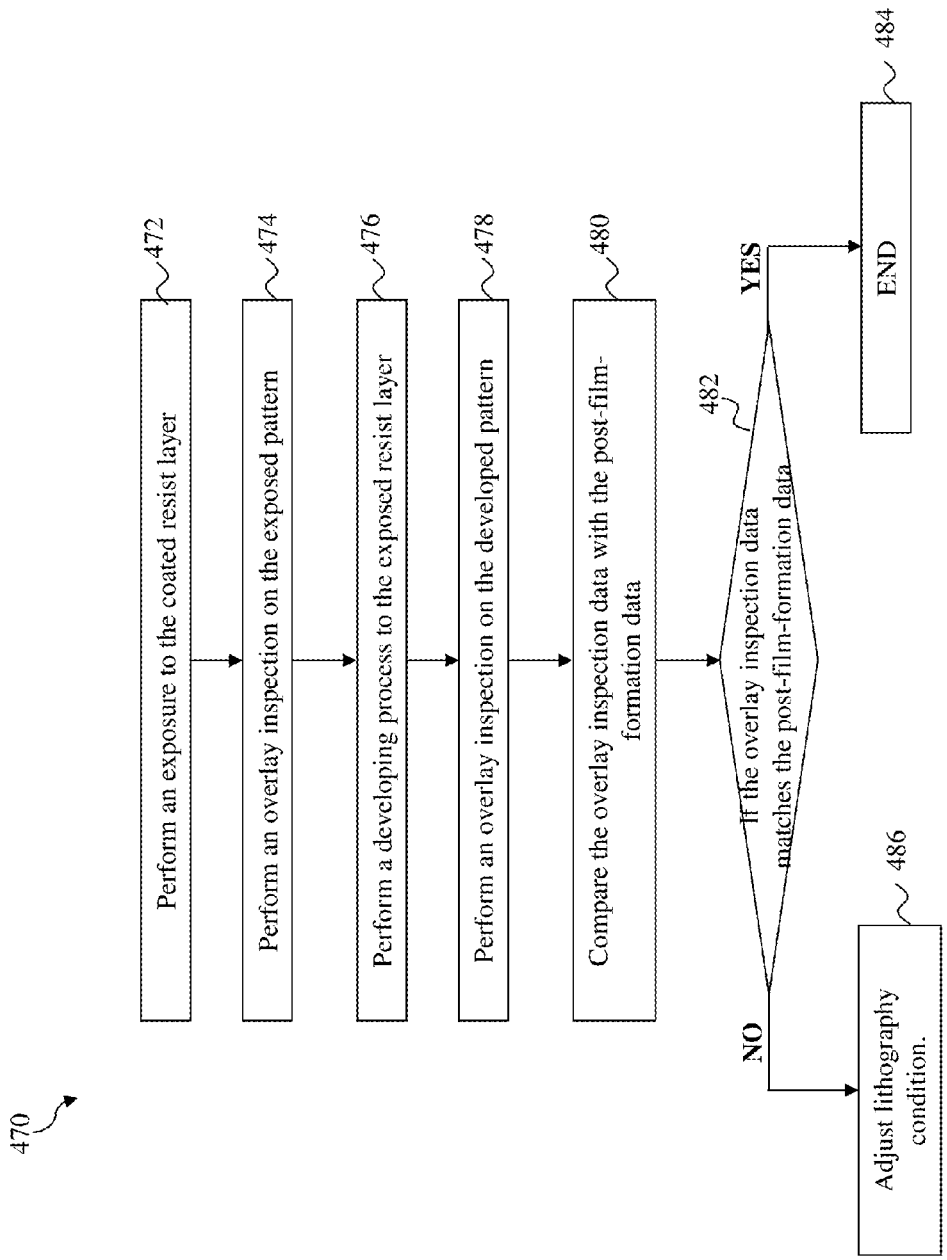
FIG. 4D is a flowchart of a method for comparing post-film-formation data with inspection data after patterning a coated resist layer using the semiconductor fabrication systems of FIG. 1 according to aspects of the present disclosure in one or more embodiments.

FIG. 4D is a flowchart of a method 470 for comparing the post-film-formation data with the overlay inspection data measured after patterning the coated resist layer in the semiconductor structure 300. In some embodiments, the post-film-formation data may be measured and stored using method 400 or method 430 according to aspects of the present disclosure in one or more embodiments. In some embodiments, the overlay inspection data from other layers formed on the patterned layer, or the pre-film-deposition data may also be compared with the overlay inspection data in method 470.

Method 470 starts from step 472 by performing an exposure process to the coated resist layer to transfer IC patterns from the lithography mask to the resist layer coated on the wafer. The exposure process is performed using the exposure tool 112 of system 100. In some embodiments after exposing the resist layer, a post exposure baking (PEB) is performed to the exposed resist layer using the baking module 108 of the lithography track unit 104.

Method 470 proceeds to step 474 by performing an overlay inspection on the exposed layer to determine the overlay error between the exposed resist layer and the underlying film layers of the semiconductor structure. In some embodiments, the overlay inspection at step 474 is performed by the overlay inspection tool 122 of the scanner 128. In some embodiments, the overlay inspection at step 474 is performed by the inspection unit 114. During the exposure process, one or more marks on the lithography mask are transferred to the patterned resist layer. In some embodiments, before the following developing process, the overlay inspection data of the exposed resist layer is compared with the post-film-formation data measured and stored by method 400 or method 430. In some embodiments, the overlay inspection data at step 474 is stored in a computer readable media and provided to the control unit 126 via network 130.

Method 470 proceeds to step 476 by performing a developing process to the exposed resist layer to form a patterned resist layer. In some examples, the developing process is performed using the development module 110 of the lithography track unit 104.

Method 470 proceeds to step 478 by performing an overlay inspection on the patterned resist layer (a post-pattern overlay inspection). In some embodiments, the overlay inspection is implemented by the overlay inspection tool 122 of the scanner 128 for measuring the overlay errors between the patterned resist layer and the underlying film layer of the semiconductor structure 300. In some embodiments, the overlay inspection at step 474 is performed by the inspection unit 114. In some embodiments, the one or more marks transferred from the lithography mask to the patterned resist layer are compared with the overlay inspection data (e.g., post-film-formation data) measured and stored by method 400 or method 430. In some embodiments, the overlay inspection data at step 478 (post-pattern overlay data) is stored in a computer readable media and provided to the control unit 126 via the network 130.

Method 470 proceeds to step 480 by comparing the overlay inspection data with the overlay inspection data that are measured and stored using method 400 or method 430 as discussed earlier in the present disclosure. In some embodiments, the overlay inspection data are post-film-formation data that are measured after the one or more film layers are formed on the patterned layer and before the semiconductor structure 300 is transferred to the lithography track unit 104 for the lithography process. In some embodiments, the post-film-formation data is obtained using the DF overlay inspection tool or the BF overlay inspection tool. In some embodiments, the post-pattern overlay data is compared with the post-film-formation data at step 480.

Method 470 proceeds to step 482 by determining if the overlay inspection data from step 480 matches the post-film-formation data. When the overlay inspection data matches the post-film-formation data, step 482 proceeds to step 484 to the end of the lithography process. One or more steps may be performed after step 484, such as etching, depositing, and/or planarizing.

When the overlay inspection data does not match the post-film-formation data, step 482 proceeds to step 486 by adjusting the lithography condition. In some examples, the control module 126 process the overlay inspection data from step 474 and/or step 478, and provide instructions via the network 130 for adjusting the parameters and/or conditions of the lithography tracking unit 104, such as the baking module 108 and/or the development module 110, for compensating the error. In some examples, the control module 126 may send instructions for adjusting the parameters of the exposure tool 112 or adjust the conditions for the exposing process.

Although various embodiments of the system 100 and the related method utilizing the same are provided according to various aspects of the present disclosure, other alternatives and modifications may be used without departure of the spirit of the present disclosure. In some embodiments, each unit of the system 100 may stand alone. In some embodiments, each unit of the system 100 may be distributed into different modules from what is shown in FIG. 1. In one embodiment, the semiconductor fabrication system may also incorporate other techniques and components. For example, the semiconductor fabrication system may also include components and mechanism to implement an immersion lithography process. In another example, if the radiation energy is EUV beam, the optical lens and the masks are reflective components. By utilizing the semiconductor fabrication system and implementing various disclosed methods, one or more advantages may present in different embodiments. In one example, the image contrast can be greatly improved using the DF inspection tool. Therefore, the alignment measurement and the overlay inspection are more convenient and accurate.

The present disclosure provides an embodiment of a method for fabricating a semiconductor structure. The method comprises providing a substrate and a patterned layer formed on the substrate, one or more overlay marks being formed on the patterned layer; performing a pre-film-formation overlay inspection using a bright field (BF) inspection tool to receive a pre-film-formation data on the one or more overlay marks on the patterned layer; forming one or more layers on the patterned layer; performing a post-film-formation overlay inspection using a dark field (DF) inspection tool to receive a post-film-formation data on the one or more overlay marks underlying the one or more layers; and determining whether the pre-film-formation data matches the post-film-formation data.

In some embodiments, before performing the post-film-formation overlay inspection using the DF inspection tool, the method further comprises performing the post-film-formation overlay inspection using the BF inspection tool.

In some embodiments, the method further comprises determining whether a number of the overlay marks in the pre-film-formation data matches a number of the overlay marks in the post-film-formation data measured using the BF inspection tool; and when the number of the overlay marks in the pre-film-formation data does not match the number of the overlay marks in the post-film-formation data measured using the BF inspection tool, performing the post-film-formation overlay inspection using the DF inspection tool.

In some embodiments, determining whether the pre-film-formation data matches the post-film-formation data comprises determining whether a number of the overlay marks in the pre-film-formation data matches a number of the overlay marks in the post-film-formation data.

In some embodiments, determining whether the pre-film-formation data matches the post-film-formation data comprises determining whether positions of the overlay marks in the pre-film-formation data match positions of the overlay marks in the post-film-formation data.

In some embodiments, when the positions of the overlay marks in the pre-film-formation data does not match the positions of the overlay marks in the post-film-formation data, the method further comprises adjusting film formation conditions for forming the one or more layers.

In some embodiments, when the pre-film-formation data matches the post-film-formation data, the method further comprises coating a resist layer on the one or more layers; and performing a post-coating overlay inspection on the coated resist layer to receive a post-coating overlay data.

In some embodiments, the method further comprises determining whether the post-coating overlay data matches the post-film-formation data.

In some embodiments, when the post-coating overlay data matches the post-film-formation data, the method further comprises performing an exposure to the coated resist layer.

In some embodiments, when the post-coating overlay data does not match the post-film-formation data, the method further comprises adjusting lithography conditions.

In some embodiments, the method further comprises performing a developing process to the exposed resist layer.

In some embodiments, the method further comprises performing a post-pattern overlay inspection to receive a post-pattern overlay data; and determining whether the post-pattern overlay data match the post-film-formation data.

In some embodiments, when the post-pattern overlay data does not match the post-film-formation data, the method further comprises adjusting lithography conditions.

The present disclosure also provides an embodiment of a method for fabricating a semiconductor structure. The method comprises providing a substrate and a patterned layer formed on the substrate, one or more overlay marks being formed on the patterned layer; performing a pre-film-formation overlay inspection using a bright field (BF) inspection mode of an inspection tool to receive a pre-film-formation data on the one or more overlay marks on the patterned layer; forming a first layer on the patterned layer; performing a first overlay inspection using a dark field (DF) inspection tool to receive a first data on the one or more overlay marks underlying the first layer; and determining whether the pre-film-formation data matches the first data.

In some embodiments, when the pre-film-formation data matches the first data, the method further comprises determining whether a second layer is to be formed on the first layer.

In some embodiments, when the pre-film-formation data does not match the first data, the method further comprises adjusting film formation conditions.

In some embodiments, when the second layer is not to be formed on the first layer, the method further comprises coating a resist layer on the first layer.

In some embodiments, when the second layer is to be formed on the first layer, the method further comprises forming the second layer on the first layer; performing a second overlay inspection suing the DF inspection tool to receive a second data on the one or more overlay marks underlying the first layer and the second layer; determining whether the pre-film-formation data matches the second data.

The present disclosure also provides yet another embodiment of a system for inspecting overlay marks. The system comprises a network; a film fabrication unit coupled to the network and configured to form one or more film layers on a patterned layer, the patterned layer including one or more overlay marks; a lithography tool coupled to the network and configured to form a patterned resist layer on the one or more film layers; an inspection unit coupled to the network, and a control unit coupled to the network. The inspection unit includes a bright field (BF) overlay inspection tool coupled to the network and configured to perform a BF overlay inspection on the one or more overlay marks on the patterned layer; and a dark field (DF) overlay inspection tool coupled to the network and configured to perform a DF overlay inspection on the one or more overlay marks underlying the one or more film layers. The control unit is configured to receive overlay inspection data from the DF and BF overlay inspection tools, a post-coating overlay data, and a post-pattern overlay data of the patterned resist layer on the one or more film layers; compare the overlay inspection data to the post-coating overlay data; and compare the overlay inspection data to the post-pattern overlay data.

In some embodiments, the lithography tool includes a lithography track unit and a scanner.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method for fabricating a semiconductor structure, comprising:
   providing a substrate and a patterned layer formed on the substrate, one or more overlay marks being formed on the patterned layer;
   performing a pre-film-formation overlay inspection using a bright field (BF) inspection tool to receive a pre-film-formation data on the one or more overlay marks on the patterned layer;
   forming one or more layers on the patterned layer;
   performing a post-film-formation overlay inspection using a dark field (DF) inspection tool to receive a post-film-formation data on the one or more overlay marks underlying the one or more layers; and
   determining whether the pre-film-formation data matches the post-film-formation data.

2. The method of claim 1, before the performing the post-film-formation overlay inspection using the DF inspection tool, further comprising:
   performing the post-film-formation overlay inspection using the BF inspection tool.

3. The method of claim 2, further comprising:
   determining whether a number of the overlay marks in the pre-film-formation data matches a number of the overlay marks in the post-film-formation data measured using the BF inspection tool; and
   when the number of the overlay marks in the pre-film-formation data does not match the number of the overlay marks in the post-film-formation data measured using the BF inspection tool, performing the post-film-formation overlay inspection using the DF inspection tool.

4. The method of claim 1, wherein the determining whether the pre-film-formation data matches the post-film-formation data comprises determining whether a number of the overlay marks in the pre-film-formation data matches a number of the overlay marks in the post-film-formation data.

5. The method of claim 1, wherein the determining whether the pre-film-formation data matches the post-film-formation data comprises determining whether positions of the overlay marks in the pre-film-formation data match positions of the overlay marks in the post-film-formation data.

6. The method of claim 5, further comprising:
when the positions of the overlay marks in the pre-film-formation data do not match the positions of the overlay marks in the post-film-formation data, adjusting film formation conditions for forming the one or more layers.

7. The method of claim 1, further comprising:
when the pre-film-formation data matches the post-film-formation data, coating a resist layer on the one or more layers; and
performing a post-coating overlay inspection on the coated resist layer to receive a post-coating overlay data.

8. The method of claim 7, further comprising:
determining whether the post-coating overlay data matches the post-film-formation data.

9. The method of claim 8, when the post-coating overlay data does not match the post-film-formation data, further comprising:
adjusting lithography conditions.

10. The method of claim 8, when the post-coating overlay data matches the post-film-formation data, further comprising:
performing an exposure to the coated resist layer.

11. The method of claim 10, further comprising:
performing a developing process to the exposed resist layer.

12. The method of claim 11, further comprising:
performing a post-pattern overlay inspection to receive a post-pattern overlay data; and
determining whether the post-pattern overlay data match the post-film-formation data.

13. The method of claim 12, when the post-pattern overlay data does not match the post-film-formation data, further comprising:
adjusting lithography conditions.

14. A method for fabricating a semiconductor structure, comprising:
providing a substrate and a patterned layer formed on the substrate, one or more overlay marks being formed on the patterned layer;
performing a pre-film-formation overlay inspection using a bright field (BF) inspection mode of an inspection tool to receive a pre-film-formation data on the one or more overlay marks on the patterned layer;
forming a first layer on the patterned layer;
performing a first overlay inspection using a dark field (DF) inspection tool to receive a first data on the one or more overlay marks underlying the first layer; and
determining whether the pre-film-formation data matches the first data.

15. The method of claim 14, when the pre-film-formation data matches the first data, further comprising:
determining whether a second layer is to be formed on the first layer.

16. The method of claim 14, when the pre-film-formation data does not match the first data, further comprising:
adjusting film formation conditions.

17. The method of claim 15, when the second layer is not to be formed on the first layer, further comprising:
coating a resist layer on the first layer.

18. The method of claim 15, when the second layer is to be formed on the first layer, further comprising:
forming the second layer on the first layer;
performing a second overlay inspection suing the DF inspection tool to receive a second data on the one or more overlay marks underlying the first layer and the second layer;
determining whether the pre-film-formation data matches the second data.

19. A method for fabricating a semiconductor structure, comprising:
providing a substrate and a patterned layer formed on the substrate, one or more overlay marks being formed on the patterned layer;
performing a pre-film-formation overlay inspection using a bright field (BF) inspection tool to receive a pre-film-formation data on the one or more overlay marks;
forming a first layer on the patterned layer;
performing a post-film-formation overlay inspection using the BF inspection tool to receive a first post-film-formation data on the one or more overlay marks;
determining whether the pre-film-formation data matches the first post-film-formation data; and
when the pre-film-formation data does not match the first post-film-formation data, performing a second post-film-formation overlay inspection using a dark field (DF) inspection tool to receive a second post-film-formation data on the one or more overlay marks.

20. The method of claim 19, wherein the determining whether the pre-film-formation data matches the first post-film-formation data includes:
determining whether a number of the overlay marks in the pre-film-formation data matches a number of the overlay marks in the first post-film-formation data; and
determining whether positions of the overlay marks in the pre-film-formation data match positions of the overlay marks in the first post-film-formation data.

* * * * *